US010317491B2

(12) United States Patent
Beck et al.

(10) Patent No.: US 10,317,491 B2
(45) Date of Patent: Jun. 11, 2019

(54) NAVIGATOR-BASED MAGNETIC RESONANCE METHOD AND APPARATUS TO DETECT NON-RIGID MOTION IN LARGE JOINT MAGNETIC RESONANCE IMAGING

(71) Applicant: Siemens Healthcare GmbH, Erlangen (DE)

(72) Inventors: Thomas Beck, Erlangen (DE); Himanshu Bhat, Cambridge, MA (US)

(73) Assignee: Siemens Healthcare GmbH, Erlangen (DE)

(*) Notice: Subject to any disclaimer, the term of this patent is extended or adjusted under 35 U.S.C. 154(b) by 712 days.

(21) Appl. No.: 14/943,386

(22) Filed: Nov. 17, 2015

(65) Prior Publication Data
US 2017/0139026 A1  May 18, 2017

(51) Int. Cl.
*G01R 33/483* (2006.01)
*G01R 33/565* (2006.01)
*A61B 5/055* (2006.01)

(52) U.S. Cl.
CPC .......... *G01R 33/4835* (2013.01); *A61B 5/055* (2013.01); *G01R 33/56509* (2013.01)

(58) Field of Classification Search
CPC ........ G01R 33/56509; G01R 33/56391; G01R 33/56375; G01R 33/5673; G01R 33/5676; G01R 33/4835; A61B 5/055
See application file for complete search history.

(56) References Cited

U.S. PATENT DOCUMENTS

| 2002/0087274 A1* | 7/2002 | Alexander | A61B 5/1114 702/19 |
| 2003/0153826 A1* | 8/2003 | Jack | A61B 5/055 600/410 |
| 2014/0159724 A1* | 6/2014 | Praveen | G01R 33/54 324/309 |
| 2014/0210469 A1* | 7/2014 | Cheng | G01R 33/56509 324/309 |
| 2015/0073263 A1* | 3/2015 | Gdaniec | G01R 33/4818 600/413 |

(Continued)

OTHER PUBLICATIONS

Kober et al., "Head Motion Detection Using FID Navigators," Magnetic Resonance in Medicine, vol. 66, pp. 135-143 (2011).

(Continued)

*Primary Examiner* — Son T Le
*Assistant Examiner* — Dustin R Dickinson
(74) *Attorney, Agent, or Firm* — Schiff Hardin LLP

(57) ABSTRACT

In a magnetic resonance (MR) navigator-based method and apparatus, MR data are acquired from a large joint of a patient, which is not modelable as a whole based on a single rigid body model. The field of view which the MR data are acquired is divided in a processor into multiple sub-sections, with each sub-section being modelable based on a rigid body model. MR navigator signals are acquired from each of the sub-sections, and these navigator signals are used in a motion tracking algorithm that is based on a rigid body model in order to generate a modeling result that tracks the movement of the overall joint within the field of view. The modeling result can be used for prospective or retrospective motion correction of the MR data.

9 Claims, 2 Drawing Sheets

(56) References Cited

U.S. PATENT DOCUMENTS

2015/0265219 A1\* 9/2015 Feiweier ............... A61B 5/721
600/476

OTHER PUBLICATIONS

Tisdall et al., "Volumetric Navigators for Prospective Motion Correction and Selective Reacquisition in Neuroanatomical MRI," Magnetic Resonance in Medicine, vol. 68, pp. 389-399 (2012).

Bhat et al., "Simultaneous Multi-Slice (SMS) Accelerated EPI Navigators for Prospective Motion Correction in the Brain," Proceedings of the ISMRM 23rd Annual Meeting and Exhibition (2015) p. 5020.

Thesen et al., "Prospective Acquisition Correction for Head Motion With Image-Based Tracking for Real-Time fMRI," Magnetic Resonance in Medicine, vol. 44, pp. 457-465 (2000).

Lange et al., "Knee Cartilage MRI with In Situ Mechanical Loading Using Prospective Motion Correction," Magnetic Resonance in Medicine, vol. 71(2), pp. 516-523 (2014).

\* cited by examiner

Navigator Sub-volume 1

Imaging Volume

Navigator Sub-volume 2

NAVIGATOR-BASED MAGNETIC RESONANCE METHOD AND APPARATUS TO DETECT NON-RIGID MOTION IN LARGE JOINT MAGNETIC RESONANCE IMAGING

BACKGROUND OF THE INVENTION

Field of the Invention

The present invention concerns methods and systems for magnetic resonance imaging, and in particular concerns methods and systems for implementing motion correction in magnetic resonance imaging of large joints, such as the knee.

Description of the Prior Art

Magnetic resonance (MR) imaging is a known technology with which images from the interior of an examination subject, such as a patient, can be generated. Simply described, the examination subject is placed in a magnetic resonance imaging scanner in which a strong, static, homogenous basic magnetic field is generated, typically having a field strength of 0.2 through 7 or more Tesla, causes nuclear spins in the subject to be oriented along the field lines of the basic magnetic field. In order to trigger magnetic resonance signals, the examination subject is irradiated with radio-frequency excitation pulses (RF pulses), that cause the nuclear spins to deviate from the aligned orientation produced by the basic magnetic field. As the excited nuclear spins relax (i.e., return to the original orientation), they emit magnetic resonance signals. These magnetic resonance signals are also RF signals, and are detected by one or more suitable antennas, as raw data. The detected raw data are entered into a memory that represents a mathematical domain known as k-space and MR images are reconstructed on the basis of the k-space data, typically by a Fourier transformation of the raw data in k-space into image data. The image data are then used to display an image of the anatomy within the field of view from which the MR signals were acquired.

Motion of the patient that occurs within the field of view while the MR raw data are being acquired degrades the quality of the resulting image. Such patient motion typically leads to artifacts in the reconstructed image, such as blurring and ghosting.

Many techniques are known in the field of magnetic resonance imaging for correcting or compensating for motion that occurs within the field of view from which MR data have been acquired. Known motion compensation techniques can be generally divided into two categories: (i) prospective motion correction, wherein the imaging field of view (FOV) is updated "on the fly" during acquisition of the MR raw data, and (ii) retrospective motion correction, wherein the motion correction is performed after the acquisition of the MR raw data, i.e., during image reconstruction.

Common to both prospective and retrospective techniques is that they both require a measurement of the motion that occurs during the scan, i.e., during the acquisition of the MR raw data. Such motion detection can be performed either with MR-based techniques, (called MR navigators), or with external motion tracking systems, such as optical tracking.

MR navigator signals are resonant signals that are acquired from the subject in the MR scanner from a suitably-sized volume of the subject, which is susceptible to the motion that is being tracked. The MR navigator signals can be acquired and processed very quickly and thus are available for use during the actual acquisition of the MR data, such as for adjusting the field of view.

The use of MR-based navigators has been extensively developed for neuroimaging, and can range from acquiring one-dimensional projections in k-space, as described in the article by Kober et al. "Head Motion Detection Using FID Navigators," Magnetic Resonance in Medicine, Vol. 66, pp. 135-143 (2011) to full 3D low special resolution images acquired with techniques such as 3D EPI, as described in the article by Tisdall et al. "Volumetric Navigators for Prospective Motion Correction and Selective Reacquisition in Neuro Anatomical MRI," Magnetic Resonance in Medicine, Vol. 68, pp. 389-399 (2012). A further technique is described in Bhat et al. "Simultaneous Multi-Slice (SMS) Accelerated EPI Navigators for Prospective Motion Correction in the Brain," Proceedings of the ISMRM 23rd Annual Meeting and Exhibition (2015) p. 5020 all of these MR navigator methods rely on the assumption that the motion of the object being tracked is rigid in nature, and thus can be modeled with six degrees of freedom (three rotations and three translations). This rigid body assumption is valid in neuroimaging, wherein the brain can be assumed to be a rigidly moving object (i.e., the entire brain moves in whatever direction is detected). For MR imaging in orthopedic applications, however, such as for obtaining MR images of a knee or an elbow, this rigid body assumption is not valid.

SUMMARY OF THE INVENTION

An object of the present invention is to provide a magnetic resonance method and apparatus, and a non-transitory, computer-readable data storage medium, which allow detection of non-rigid motion in MR imaging of large joints that cannot be modeled as a whole by rigid body model.

This object is achieved in accordance with the invention in a method and apparatus wherein the MR navigator FOV is divided into multiple sub-sections, and making the assumption that the motion in each sub-section is rigid in nature. Each sub-section can then be individually tracked with known navigator-based approaches, such as the aforementioned SMS-EPI navigator approach described in the Bhat et al. article, which is an ultra-fast MR navigator technique. The SMS navigator approach makes it feasible to acquire the navigator data for all of the sub-volumes (sub-sections) rapidly, thereby making the technique practical in clinical settings.

Motion tracking for each sub-section for which a navigator signal is acquired can be done using existing techniques, such as the PACE techniques as described in the article by Thesen et al. "Prospective Acquisition Correction for Head Motion With Image-Based Tracking for Real-Time fMRI, Magnetic Resonance in Medicine, Vol. 44, pp. 457-465 (2000). Such techniques are designed for detecting rigid body motion, and thus they are applicable for the aforementioned sub-sections into which the overall FOV has been divided. The SMS navigator acquisition block is very short in duration, and can easily be embedded, with the desired temporal resolution for motion tracking, into the base MRI sequence that is being used to acquire the raw MR data from the FOV.

The motion information for each sub-section can be used to compensate for the motion within the FOV in multiple ways. For example, the tracked motion can be used in retrospective reconstruction to provide the appropriate motion fields in the reconstruction algorithm, or modifying the FOV in prospective motion correction, or for rejecting overly motion-corrupted data in real-time during the acquisition of the raw MR data or for gating that pauses the acquisition of MR signals for as long as the navigator signals detect motion that exceeds a predetermined threshold. Navigator data still will be acquired during such a pause, and when the threshold is no longer exceeded, MR data acquisition is resumed.

The non-transitory, computer-readable data storage medium in accordance with the invention is encoded with programming instructions that cause a computer, in which the storage medium is loaded, to execute the method according to the invention. The storage medium may be a disk, a memory stick, or any other type of suitable storage medium on which the programming instructions can be stored as electronically-readable code.

DESCRIPTION OF THE PREFERRED EMBODIMENTS

Figure 1:
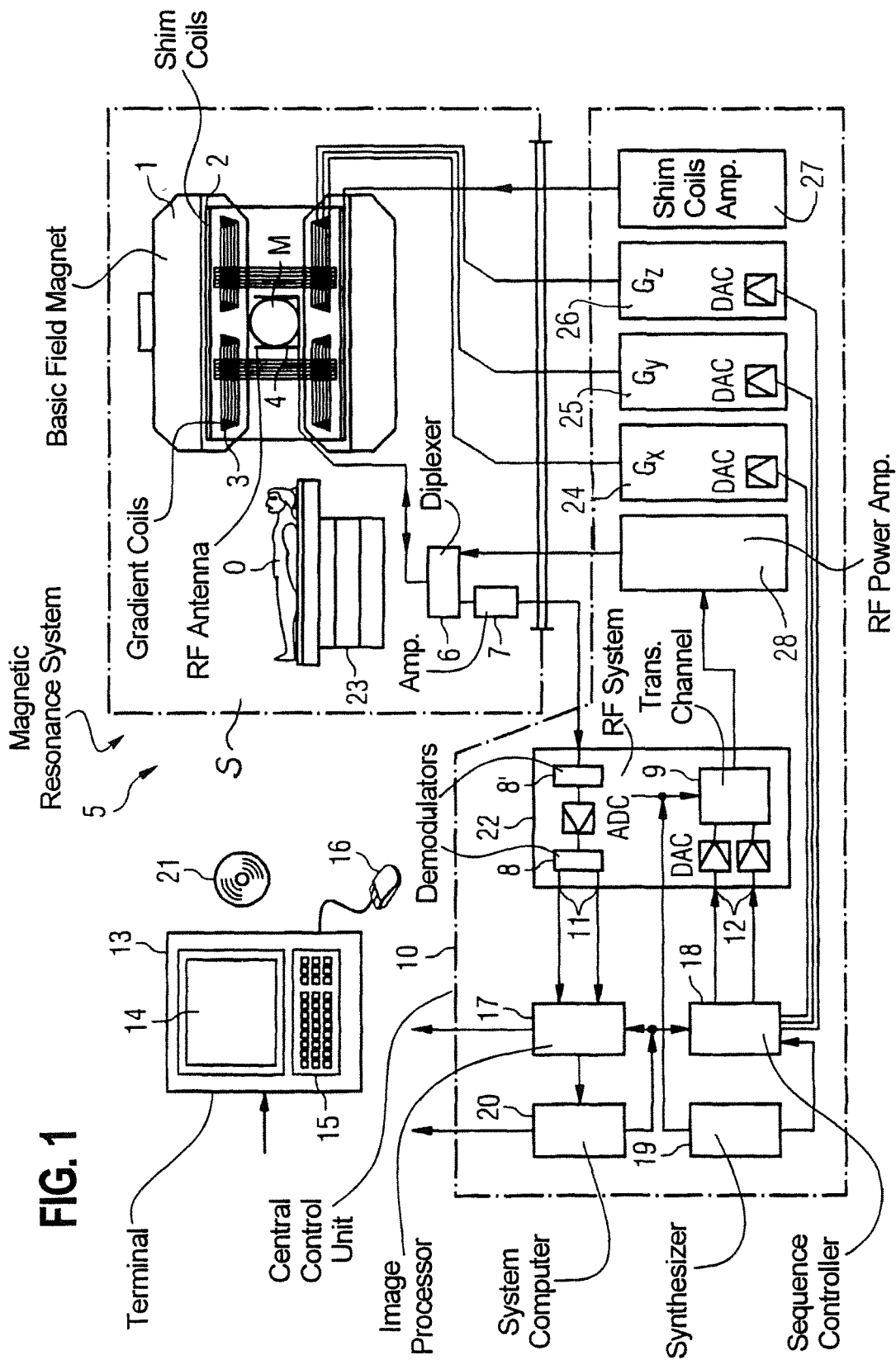
FIG. 1 is a block diagram of a magnetic resonance apparatus that is constructed and operated in accordance with the present invention.

FIG. 1 schematically illustrates a magnetic resonance apparatus 5 (a magnetic resonance imaging or tomography device). A basic field magnet 1 generates, a temporally constant strong magnetic field for the polarization or alignment of the nuclear spin in a region of an examination subject O, such as a portion of a human body that is to be examined, lying on a table 23 in order to be moved into the magnetic resonance apparatus 5. The high degree of homogeneity in the basic magnetic field necessary for the magnetic resonance measurement (data acquisition) is defined in a typically sphere-shaped measurement volume M, in which the portion of the human body that is to be examined is placed. In order to support the homogeneity requirements temporally constant effects are eliminated by shim-plates made of ferromagnetic materials are placed at appropriate positions. Temporally variable effects are eliminated by shim-coils 2 and an appropriate control unit 27 for the shim-coils 2.

A cylindrically shaped gradient coil system 3 is incorporated in the basic field magnet 1, composed of three windings. Each winding is supplied by a corresponding amplifier 24-26 with power for generating a linear gradient field in a respective axis of a Cartesian coordinate system. The first partial winding of the gradient field system 3 generates a gradient $G_x$, in the x-axis, the second partial winding generates a gradient $G_y$, in the y-axis, and the third partial winding generates a gradient $G_z$, in the z-axis. Each amplifier 24-26 has a digital-analog converter (DAC), controlled by a sequencer 18 for the accurately-times generation of gradient pulses.

A radio-frequency antenna 4 is located within the gradient field system 3, which converts the radio-frequency pulses provided by a radio-frequency power amplifier into a magnetic alternating field for the excitation of the nuclei by tipping ("flipping") the spins in the subject or the region thereof to be examined, from the alignment produced by the basic magnetic field. The radio-frequency antenna 4 is composed of one or more RF transmitting coils and one or more RF receiving coils in the form of an annular, linear or matrix type configuration of coils. The alternating field based on the precessing nuclear spin, i.e. the nuclear spin echo signal normally produced from a pulse sequence composed of one or more radio-frequency pulses and one or more gradient pulses, is also converted by the RF receiving coils of the radio-frequency antenna 4 into a voltage (measurement signal), which is transmitted to a radio-frequency system 22 via an amplifier 7 of a radio-frequency receiver channel 8, 8'. The radio-frequency system 22 furthermore has a transmitting channel 9, in which the radio-frequency pulses for the excitation of the magnetic nuclear resonance are generated. For this purpose, the respective radio-frequency pulses are digitally depicted in the sequencer 18 as a series of complex numbers, based on a given pulse sequence provided by the system computer 20. This number series is sent via an input 12, in each case, as real and imaginary number components to a digital-analog converter (DAC) in the radio-frequency system 22 and from there to the transmitting channel 9. The pulse sequences are modulated in the transmitting channel 9 to a radio-frequency carrier signal, the base frequency of which corresponds to the resonance frequency of the nuclear spin in the measurement volume. The modulated pulse sequences of the RF transmitter coil are transmitted to the radio-frequency antenna 4 via an amplifier 28.

Switching from transmitting to receiving operation occurs via a transmission-receiving switch 6. The RF transmitting coil of the radio-frequency antenna 4 radiates the radio-frequency pulse for the excitation of the nuclear spin in the measurement volume M and scans the resulting echo signals via the RF receiving coils. The corresponding magnetic resonance signals obtained thereby are demodulated to an intermediate frequency in a phase sensitive manner in a first demodulator 8' of the receiving channel of the radio-frequency system 22, and digitalized in an analog-digital converter (ADC). This signal is then demodulated to the base frequency. The demodulation to the base frequency and the separation into real and imaginary parts occurs after digitization in the spatial domain in a second demodulator 8, which emits the demodulated data via outputs 11 to an image processor 17. In an image processor 17, an MR image is reconstructed from the measurement data obtained in this manner through the use of the method according to the invention, which includes computation of at least one disturbance matrix and the inversion thereof, in the image processor 17. The management of the measurement data, the image data, and the control program occurs via the system computer 20. The sequencer 18 controls the generation of the desired pulse sequences and the corresponding scanning of k-space with control programs, in particular, in accordance with the method according to the invention. The sequencer 18 controls accurately-timed switching (activation) of the gradients, the transmission of the radio-frequency pulse with a defined phase amplitude, and the reception of the magnetic resonance signals. The time base for the radio-frequency system 22 and the sequencer 18 is provided by a synthesizer 19. The selection of appropriate control programs for the generation of an MR image, which are stored, for example, on a DVD 21, as well as other user inputs such as a desired number n of adjacent clusters, which are to collectively cover the desired k-space, and the display of the generated MR images, occurs via a terminal 13, which includes units for enabling input entries, such as, e.g. a keyboard 15, and/or a mouse 16, and a unit for enabling a display, such as, e.g. a display screen.

The components within the dot-dash outline S are commonly called a magnetic resonance scanner.

Figure 2:
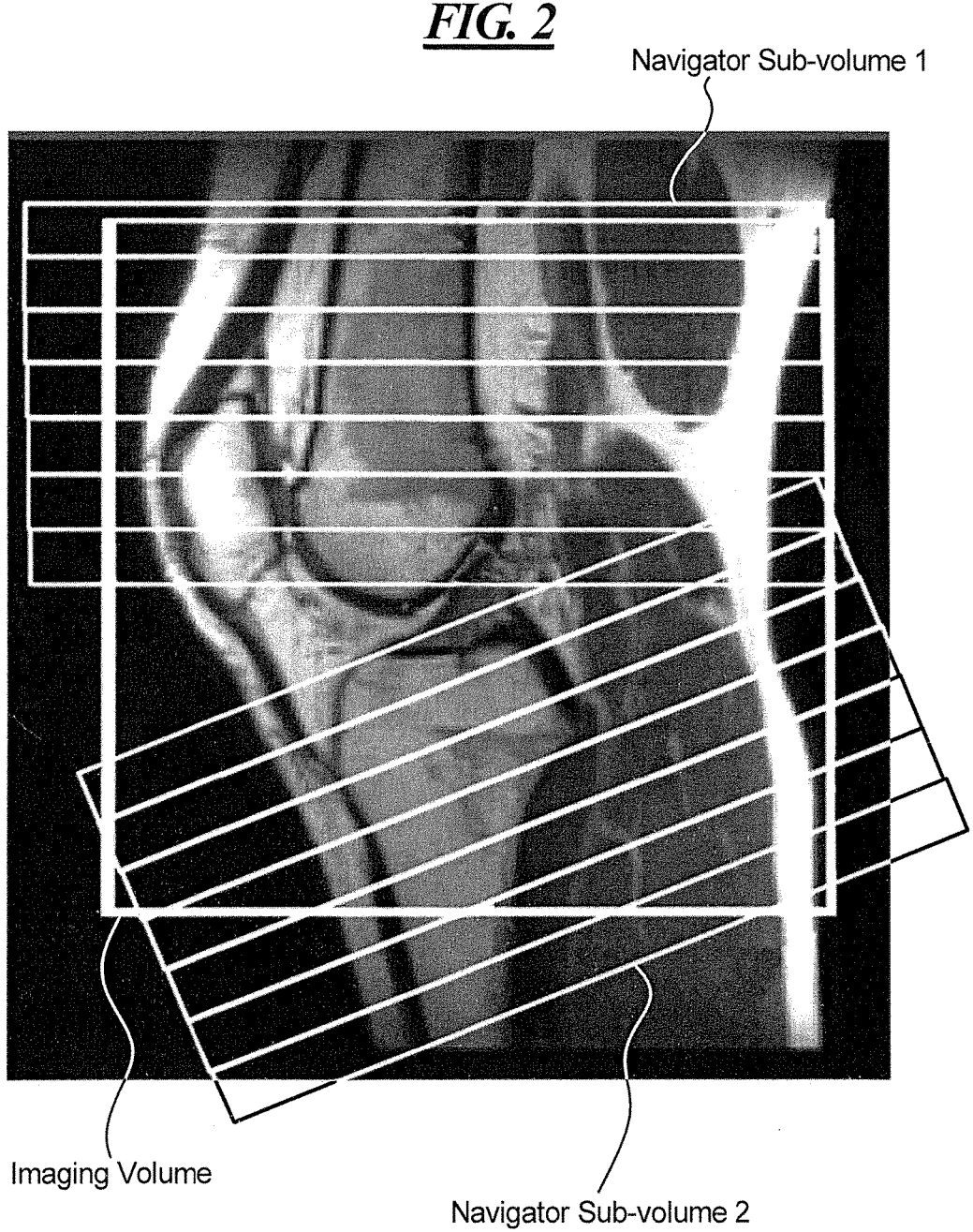
FIG. 2 schematically illustrates an embodiment of the invention, wherein the FOV is divided into two multi-slice sub-sections.

As schematically illustrated in FIG. 2, in accordance with the invention the navigator FOV is divided into multiple sub-sections. In the embodiment shown in FIG. 2, two such sub-sections are shown, each of which is, in turn, divided into multiple slices or multiple slabs, making the division suitable for an SMS-EPI navigator technique. The imaging volume FOV is independent of the navigator sub-volume such that underlying anatomy is optimally displayed.

The overall motion of the knee, which is shown within the FOV in FIG. 2, is non-rigid, but each sub-section (one above the knee joint and the other below the knee joint) can be assumed to move rigidly. This makes it suitable to use two navigator sub-volumes or sub-sections, as the multiple sub-sections.

Navigator signals from each of these two sub-sections are acquired with the SMS-EPI navigator technique, for example, and motion tracking for each sub-section can be done with techniques that are designed for detecting rigid body motion, such as the aforementioned PACE technique.

As noted above, the SMS navigator acquisition block is very short in duration, and thus can be easily embedded, with the desired temporal resolution for motion tracking, into the base MRI sequence that is used to acquire the raw MR data.

As a result of the application of the motion tracking technique using the navigator signals respectively acquired from the multiple sub-sections into which the FOV has been divided, a processor produces an electronic signal that represents the motion, which can be used in various ways. For example, the motion-tracking signal can be used in a retrospective image reconstruction in order to produce the appropriate motion fields that are needed in retrospective motion correction techniques. Alternatively or additionally, the motion information can be used to adjust the FOV "on the fly" during the MR raw data acquisition, or can be used to reject overly motion-corrupted data in real-time during the acquisition of the MR raw data or for gating that pauses the acquisition of MR signals for as long as the navigator signals detect motion that exceeds a predetermined threshold. Navigator data still will be acquired during such a pause, and when the threshold is no longer exceeded, MR data acquisition is resumed.

Although modifications and changes may be suggested by those skilled in the art, it is the intention of the inventors to embody within the patent warranted hereon all changes and modifications as reasonably and properly come within the scope of their contribution to the art.

We claim as our invention:

1. A magnetic resonance (MR) navigator-based method to detect non-rigid motion in large joint MR imaging, comprising:
   with a control computer to, operating an MR scanner while a patient is situated therein to acquire MR raw data from a field of view (FOV) of the patient exhibiting movement during the acquisition of said MR raw data;
   providing a designation of said FOV to a processor and, in said processor, dividing said FOV into multiple sub-sections that are each modelable based on a rigid body model;
   with said control computer to, operating said MR scanner to acquire MR navigator signals from each of said sub-sections;
   in said processor, using the respective navigator signals acquired from the respective sub-sections in a rigid body modeling of respective sub-sections in said multiple sub-sections, to generate a modeling result that tracks said movement of said joint in said FOV;
   in said processor, using said modeling result to generate an electronic signal that represents said movement, and providing said electronic signal to said control computer; and
   upon receipt of said electronic signal by said control computer, said control computer changing operation of said MR scanner by executing a prospective motion correction action selected from the group consisting of modifying said FOV dependent on said movement represented in said electronic signal, and pausing acquisition of said MR raw data for as long as said MR navigator signals detect a motion that exceeds a predetermined threshold, while still acquiring said MR navigator signals during each pause.

2. A method as claimed in claim 1 comprising, in said processor, executing an image reconstruction algorithm to transform said raw MR data into MR image data and using said movement of said joint in said FOV represented in said electronic signal to implement retrospective motion correction when executing said image reconstruction algorithm.

3. A method as claimed in claim 1 comprising operating said MR scanner to acquire said navigator signals with a simultaneous multi-slice echo planar imaging method.

4. A method as claimed in claim 1 comprising generating said modeling result using a prospective acquisition correction (PACE) algorithm.

5. A method as claimed in claim 1 comprising dividing said FOV into two sub-sections.

6. A method as claimed in claim 1 comprising dividing said FOV into multiple multi-slice sub-sections.

7. A method as claimed in claim 1 comprising dividing said FOV into two multi-slice sub-sections, acquiring said navigator signals with a simultaneous multi-slice echo planar imaging method, and generating said modeling result using a prospective acquisition correction (PACE) algorithm.

8. A magnetic resonance (MR) apparatus comprising:
   an MR scanner;
   a control computer configured to operate said MR scanner while a patient is situated therein to acquire MR raw data from a field of view (FOV) of the patient exhibiting movement during the acquisition of said MR raw data;
   a processor provided with a designation of said FOV, said processor being configured to divide said FOV into multiple sub-sections that are each modelable based on a rigid body model;
   said control computer being configured to operate said MR scanner to acquire MR navigator signals from each of said sub-sections;
   said processor being provided with said navigator signals and being configured to use the respective navigator signals acquired from the respective sub-sections in a rigid body modeling of respective sub-sections in said multiple sub-sections, to generate a modeling result that tracks said movement of said joint in said FOV;
   said processor being configured to generate an electronic signal that represents said movement and to provide said electronic signal to said control computer; and
   said control computer being configured to, upon receipt of said electronic signal by said control computer, change operation of said MR scanner by executing a prospective motion correction action selected from the group consisting of modifying said FOV dependent on said movement represented in said electronic signal, and pausing acquisition of said MR raw data for as long as said MR navigator signals detect a motion that exceeds a predetermined threshold, while still acquiring said MR navigator signals during each pause.

9. A non-transitory, computer-readable data storage medium encoded with programming instructions, said storage medium being loaded into a control and evaluation processor of a magnetic resonance (MR) apparatus that also comprises an MR scanner, said programming instructions causing said control and evaluation processor to:

operate the MR scanner while a patient is situated therein to acquire MR raw data from a field of view (FOV) of the patient that encompasses a joint exhibiting movement during the acquisition of said MR raw data;

divide said FOV into multiple sub-sections that are each modelable based on a rigid body model;

operate said MR scanner to acquire MR navigator signals from each of said sub-sections;

use the respective navigator signals acquired from the respective sub-sections in a rigid body modeling of respective sub-sections in said multiple sub-sections, to generate a modeling result that tracks said movement of said joint in said FOV;

generate an electronic signal that represents said movement; and in response to said electronic signal, change operation of said MR scanner by executing a prospective motion correction action selected from the group consisting of modifying said FOV dependent on said movement represented in said electronic signal, and pausing acquisition of said MR raw data for as long as said MR navigator signals detect a motion that exceeds a predetermined threshold, while still acquiring said MR navigator signals during each pause.

* * * * *